United States Patent
Chen et al.

(10) Patent No.: US 8,309,035 B2
(45) Date of Patent: Nov. 13, 2012

(54) MULTI-WELL SYSTEM

(75) Inventors: Chun-Nan Chen, San Jose, CA (US); James O. Bowlby, Jr., San Jose, CA (US); Richard Aleck Jorgensen, San Jose, CA (US)

(73) Assignee: Single Cell Technology, Inc., San Jose, CA (US)

( * ) Notice: Subject to any disclaimer, the term of this patent is extended or adjusted under 35 U.S.C. 154(b) by 557 days.

(21) Appl. No.: 12/418,520

(22) Filed: Apr. 3, 2009

(65) Prior Publication Data

US 2009/0280992 A1 Nov. 12, 2009

Related U.S. Application Data

(60) Provisional application No. 61/072,985, filed on Apr. 5, 2008, provisional application No. 61/141,579, filed on Dec. 30, 2008.

(51) Int. Cl. *G01N 21/75* (2006.01)

(52) U.S. Cl. ....................................................... 422/407

(58) Field of Classification Search .................. None
See application file for complete search history.

(56) References Cited

U.S. PATENT DOCUMENTS

| | | | |
|---|---|---|---|
| 4,642,284 A | 2/1987 | Cooper et al. | |
| 5,110,556 A | 5/1992 | Lyman et al. | |
| 6,083,682 A * | 7/2000 | Campbell et al. | 435/4 |
| 6,083,683 A * | 7/2000 | Pace et al. | 435/4 |
| 6,087,103 A | 7/2000 | Burmer | |
| 6,091,001 A | 7/2000 | Jakobovits | |
| 6,232,066 B1 | 5/2001 | Felder et al. | |
| 6,329,139 B1 * | 12/2001 | Nova et al. | 506/30 |
| 6,548,263 B1 | 4/2003 | Kapur et al. | |
| 6,565,813 B1 * | 5/2003 | Garyantes | 422/553 |
| 6,746,845 B2 | 6/2004 | Kinzler et al. | |
| 6,872,576 B1 | 3/2005 | McIntyre | |
| 7,776,553 B2 | 8/2010 | Love | |
| 2002/0192673 A1 * | 12/2002 | Labaer et al. | 435/6 |
| 2003/0022194 A1 | 1/2003 | Erlander et al. | |
| 2003/0064386 A1 * | 4/2003 | Karaki et al. | 435/6 |
| 2003/0124129 A1 | 7/2003 | Oliner | |
| 2004/0185439 A1 | 9/2004 | Kalush et al. | |
| 2005/0123563 A1 | 6/2005 | Doranz et al. | |
| 2005/0142539 A1 | 6/2005 | Herman | |
| 2005/0182242 A1 | 8/2005 | Snyder et al. | |
| 2006/0134704 A1 | 6/2006 | Muraguchi et al. | |
| 2006/0177868 A1 | 8/2006 | Okakmoto et al. | |
| 2006/0269969 A1 | 11/2006 | Angelides | |
| 2007/0148690 A1 | 6/2007 | Shao et al. | |
| 2007/0161009 A1 | 7/2007 | Kohne | |
| 2007/0238089 A1 | 10/2007 | Rosenthal et al. | |
| 2008/0004185 A1 | 1/2008 | Labgold | |
| 2008/0090239 A1 | 4/2008 | Shoemaker et al. | |
| 2009/0088336 A1 * | 4/2009 | Burd et al. | 506/9 |
| 2009/0117555 A1 | 5/2009 | Kuypers et al. | |
| 2010/0035763 A1 * | 2/2010 | Chen et al. | 506/9 |
| 2011/0190148 A1 * | 8/2011 | Chen et al. | 506/9 |

FOREIGN PATENT DOCUMENTS

WO WO 2007/076580 7/2007

* cited by examiner

*Primary Examiner* — Ann Lam
(74) *Attorney, Agent, or Firm* — Convergent Law Group LLP

(57) ABSTRACT

A multi-well system is described which is comprised of a tray comprising a plurality of wells which may include thousands, tens of thousands or even hundreds of thousands of wells or more. Each of the wells has a unique address. The system includes a tray top comprised of a plurality of areas wherein each of the areas corresponds uniquely to each of the wells and includes a unique address. The system may include a second tray top also comprised of a plurality of areas with unique addresses which uniquely correspond to each of the wells. The areas on the tops have compounds bound to those areas which compounds bind to components present in the wells and are used to obtain specific material in each well for analysis.

14 Claims, 8 Drawing Sheets

SEQUENCE LISTING

```
<160> NUMBER OF SEQ ID NOS: 2

<210> SEQ ID NO 1
<211> LENGTH: 74
<212> TYPE: DNA
<213> ORGANISM: mus musculus
<220> FEATURE:
<221> NAME/KEY: variation
<222> LOCATION: (34)...(47)
<223> OTHER INFORMATION: n = a or g or t or c
<220> FEATURE:
<221> NAME/KEY: modified_base
<222> LOCATION: 68
<223> OTHER INFORMATION: n = I

<400> SEQUENCE: 1
aaaaaactcg aggccttgcc agcccgctca gatnnnnnnn nnnnnnncag gggccagtgg        60
atagactnga tggg                                                         74

<210> SEQ ID NO 2
<211> LENGTH: 85
<212> TYPE: DNA
<213> ORGANISM: mus musculus
<220> FEATURE:
<221> NAME/KEY: variation
<222> LOCATION: (34)...(47)
<223> OTHER INFORMATION: n = a or g or t or c

<400> SEQUENCE: 2
aaaaaactcg aggcctccct cgcgccatca gatnnnnnnn nnnnnnnctc cagatgttaa        60
ctgctcactg gatggtggga agatg                                             85
```

MULTI-WELL SYSTEM

CROSS-REFERENCE

This application claims the benefit of U.S. Provisional Application Nos. 61/072,985, filed Apr. 5, 2008 and 61/141,579, filed Dec. 30, 2008, which applications are incorporated herein by reference. This application is related to two other applications filed concurrently herewith on Apr. 3, 2009 which two applications have Ser. Nos. 12/418,519 and 12/418,521, which two related applications are incorporated herein by reference in their entirety.

FIELD OF THE INVENTION

This invention generally relates to multi-well devices. More specifically, the invention relates to multi-well systems which are utilized to handle and organize biological materials and more particularly to organize individual cells and extract information from those cells.

BACKGROUND OF THE INVENTION

It is often been necessary to collect various biological specimens such a whole blood, plasma, serum, CFS, feces, urine, cultured cells, saliva, cervical or urethral swab, sputum and other biological fluids. Multiple individual samples are collected and transported to a laboratory where personnel conduct specific tests on the samples. It is imperative that the biological samples be properly contained, enclosed and identified to permit the safe transport of the sample.

Collected samples must be adequately isolated, packaged and identified to permit the safe, efficient and identifiable transport of the samples to the laboratory while preventing contamination of the samples. It is therefore desirable to provide an improved packaging which allows for the collection transport and dispensing of individual discrete samples from a plurality of collected samples.

There are a number of different systems which are used for holding biological samples. One of those systems is a multi-well tray or plate. Typical multi-well trays include 96 wells each of which holds a different biological sample. There are also trays which hold larger numbers of samples in larger numbers of wells. Further, some trays are designed to incorporate micro-wells which hold very small amounts of materials such as a single cell. Because the wells are very small it is possible to include a large number of wells in a relatively small area. The present invention utilizes well trays which include very large numbers of wells in a very small area in combination with other components which make it possible to analyze the materials within the wells efficiently and accurately.

SUMMARY OF THE INVENTION

The multi-well system of the invention is comprised of a well tray. The tray is comprised of a basic frame with a plurality of wells. The wells may be organized in any manner but are preferably configured in rows and columns with each of the wells having a unique address. Although the wells may have different sizes they may be configured so that each well holds a single biological cell such as B cell or plasma cell producing antibodies. The wells may have a unique chemical tag placed therein which tag may be a nucleotide sequence bound to its surface. Although the tray may include any number of wells the system is adaptable for including tens of thousands or more, hundreds of thousands or more or even a million or more wells wherein each well is designed to hold a single cell and each well has a unique address.

A second component of the system is a well top which top may be a planar object configured to fit over the multi-well tray. The top is comprised of a plurality of areas wherein each of the areas corresponds uniquely to one of the wells. The areas may include unique addresses corresponding to each area and relatable to a unique well. Each area has bound to its surface a compound uniquely designed for binding to a component within the well. As an example each area may have bound to its surface a protein such as protein A which binds antibodies. The top is configured such that when it is placed over the well tray after which antibody producing cells in the wells are allowed to produce antibodies. The antibodies in the wells will bind to the protein on the surface of the top. The top can then be analyzed such as by determining the ability of the antibodies in a unique area to bind to a particular antigen. Each area may comprise a protuberance coated with a binding agent such as protein A.

The system may include a second top which is also comprised of a plurality of areas which uniquely correspond to the wells in the well tray and which include unique addresses each of which is related to a unique well address. The second top includes a plurality of binding agents which are different from the binding agents on the first top and which bind to a second component of cells in the well. For example, the second top can be used after the first top and may be designed to include nucleotide sequences which bind to nucleotide sequences in cells which have been lysed in the tray. The second tray may also include protuberances extending from each area and the protuberance may have a binding agent such as a nucleotide sequence bound to its surface.

The system can include a plurality of tops wherein each of the tops includes a plurality of areas (and may include protuberances from each area) with unique addresses which addresses relate to unique wells on the well tray. The different tops may include the same or different binding agents on each of the unique areas making it possible to extract different information from the cells in the wells of the well tray.

The system may further include a mechanism for precisely aligning each well top with a well in the well area. The system may clamp the top in place and include gears which make it possible to precisely position the top in three-dimensional space relative to the wells of the well tray.

The multi-well system may be used in a methodology which makes it possible to select from a very large number of cells, a single cell or cells of interest and obtain specific information from those cells in a rapid and efficient manner. As an example of the methodology, a large number of antibody producing cells such as B cells are separated so that these individual antibody producing B cells are placed in individual wells. The cells are allowed to produce antibodies and the antibodies in the wells are then contacted with a protein bound to a membrane which protein binds antibodies in the wells. The membrane includes addresses configured such that each address is specifically related to one of the individual wells containing a cell producing antibodies.

Information relating to the antibodies on the membrane is then obtained. The information can be the binding affinity of the antibodies at a particular address for a particular known antigen. The information at all of the addresses is analyzed in order to find the address or particular group of addresses which are of particular interest such as antibodies with a high binding affinity to the particular known antigen. After identifying the addresses of the antibodies of interest those addresses are correlated to the well or wells of interest.

Information relating to the DNA sequence of the antibodies is then obtained and correlated with said antibodies of interest. This is obtained by lysing the cells and isolating antibody specific mRNA.

After isolating mRNA the mRNA is used to produce cDNA. The cDNA may be sequenced and the cDNA may be used to genetically engineer cells which produce antibodies of interest. Included in the cDNA are specific tags that correlate the physical location of wells, the physical location of antibodies on said membrane, and the DNA sequence. Said specific tags allow the pooling of cDNA from all wells for subsequent determination of the individual cDNA sequences. The sequences of particular interest are those encoding the light and heavy chain variable regions or portions thereof sufficiently large to construct an antibody of interest. The sequences of the light and heavy chain of each antibody are associated using said specific tags.

The methodology can be used with hundreds, thousands, tens of thousands, hundreds of thousands or millions or cells or more at the same time. The multi-well system makes it possible to sort through large numbers of cells quickly and identify those cells which produce antibodies of interest and relate those antibodies directly to the nucleotide sequence responsible for producing the antibodies desired. The multi-well system also makes it possible to carry out an efficient method for analyzing a large number of cells with respect to the cis and/or trans-protein complexes confined to each individual cell. As such, the present invention solves the problem of reporting the average measurement for a population of cells. Briefly, cells are separated and processed in small microwells where diffusion of molecules among micro-wells is retarded or blocked. On the other hand, each micro-well, due to its small dimensions, facilitates rapid reaction rates, such as mRNA hybridization or capture of proteins. After disruption of each cell, mRNAs from target genes are captured by oligonucleotide probes located inside each micro-well. Simultaneously, corresponding protein(s) or protein complexes are retained by a capture agent confined to each micro-well. Conversion of said captured mRNA into double-stranded cDNA incorporates an oligonucleotide tag unique to each micro-well. Said cDNA can then be pooled and sequenced by ultra-high throughput DNA sequencing technology to determine the structure of each member of the protein complex in each originating cell. Said captured proteins form an array on a substrate where their kinetic properties can be analyzed when contacting with labeled affinity ligands common to all captured proteins or complexes. Such measured kinetic properties can be used to a) rank the protein complexes with respect to affinity b) filter DNA sequence data thereby removing contaminating or irrelevant cells from consideration, c) classify the type of cell based on the quantity of captured antibodies, or d) measure the frequency of cells producing similar protein complexes.

Thus, by measuring the number of cells that produce a particular protein it is possible to determine various characteristics of the protein. For example, if the protein is an antibody which might be produced in response to a particular antigen, it is possible to determine additional information which may be useful in characterizing desirable antibodies.

In one of the embodiments, the protein complex under study can be the heavy chain and light chain of an antibody. In this case, integrating structural information with kinetic properties provides insights into the paratopes on the antibody as well as the epitopes on the antigen. To illustrate this utility of the present invention, simulation with antibodies against the hapten 2-phenyl-5-oxazolone (phOX) was performed.

The present invention has many potential uses but a major application is likely to be the analysis of gene combinations that are polymorphic within a population of cells, such as the rearranged genes for Ig or T cell receptors, or cells secreting Ig, or a protein complex formed by splice variants of multiple genes potentially between normal and cancerous cells An aspect of the invention is a well tray with well openings which facilitate placing a single cell within each well wherein the tray includes tens of thousands or more, hundreds of thousands or more, or millions of wells or more.

Another aspect of the invention is that the system can be readily utilized to obtain information from each cell relating to compounds produced by the cell and then relate that information to genetic material in the cell.

Another aspect of the invention is that the multi-well system can be used to quickly analyze a very large number of B cells or plasma cells for antibodies which have a desired binding affinity for a particular antigen and then relate that information to the genetic material encoding those antibodies.

These and other objects, advantages, and features of the invention will become apparent to those persons skilled in the art upon reading the details of the methods and embodiments of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
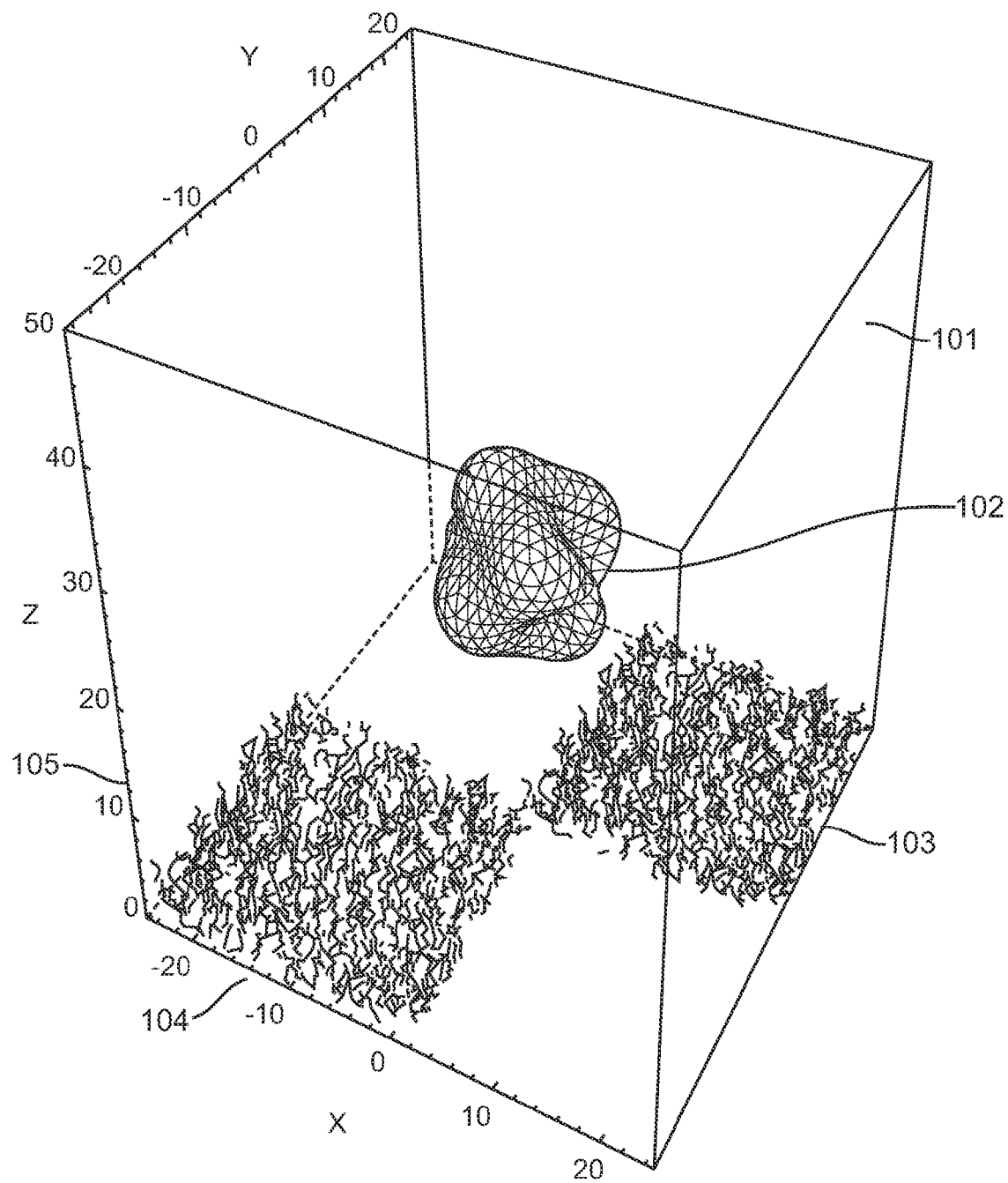
FIG. 1 is a schematic representation of a B cell or plasma cell captured in a micro-well.

As used herein, the terms "tag(s)" or, "oligonucleotide tag(s)" refer to an oligonucleotide whose sequence identifies the physical location of its origin.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'.-0.3° order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

As used herein, "hybridization" refers to the process wherein cellular RNA or single stranded DNA interacts with oligonucleotides having substantial sequence complementarity, wherein duplexes are formed in said regions of sequence complementarity.

As used herein, "micro-well" refers to sub millimeter structures with a volume between 1 picoliter and 500 nanoliters. The micro-well is typically constructed in a shape that allows dense packing on a planar substrate, i.e.: the shape is triangular, rectangular, or hexagonal. Micro-wells can be either opened by removing one surface, usually at the top, or closed by placing said top in contact with other surfaces. The micro-well can be homogeneous, or constructed out of dissimilar materials, including but not limited to glass, photoresist, or polydimethylsiloxane (PDMS).

As used herein, "paratope" refers to the part of an antibody that recognizes the epitope of an antigen.

The term "monoclonal antibody" relates to an antibody chosen from a mixture of different antibodies. All monoclonal antibodies of the same specificity are identical except for natural mutants thereof. Under the term "antibody" intact molecules of immunoglobulins as well as fragments thereof (Fab, F(ab'), Fv, scFv) are to be understood.

As used herein, a "ligand" is a substance that is able to bind to and form a complex with a biomolecule to serve a biological purpose.

The term "B cell" is used herein to mean an immune cell that develops in the bone marrow and is highly specialized for making immunoglobins and antibodies. A B cell is a lymphocyte which is derived from bone marrow and provides humoral immunity. A B cell recognizes antigen molecules in solution and matures into a plasma cell. Thus, when the term "B cell" is used herein it is intended to encompass cells developed from B cells such as plasma cells.

The term "plasma cell" is intended to mean a cell that develops from a B lymphocyte in reaction to a specific antigen. Plasma cells are found in bone marrow and blood. A plasma cell may also be called a plasma B cell or plasmacyte and are cells in the immune system which secrete large amounts of antibodies. Plasma cells differentiate from B cells upon stimulation by CD4+ lymphocytes. A plasma cell is a type of white blood cell that produces antibodies and is derived from an antigen-specific B cell. Throughout this application the term "B cell" is intended to encompass "plasma cells" and vice versa. In general both are intended to encompass terms referring to cells which produce antibodies of interest.

The term "protein complex" is used to refer to a bound collection of two or more proteins formed by protein-protein interactions that may or may not involve formation of covalent bonds. Protein complexes are a form of quaternary structure. An example is IgG, which is formed by a heavy chain and a light chain. In this case, there are disulfide linkages between the heavy and light chains. Protein complexes that are formed by proteins deriving from the same cell are referred to as "cis protein complexes". As such, IgG is an example of a cis protein complex. In contrast, protein complexes that are formed by proteins deriving from different cells or different origins are referred to as "trans protein complexes." An example of a trans protein complex is an antibody-antigen complex. The present invention relates to both cis and trans protein complexes.

As used herein, "kinetic properties" refer to the rates of reaction $k_{off}$, $k_{on}$, and their ratio $K_D$ between cis and/or trans protein complexes. For a binary protein complex, the dissociation constant $K_D$ is monotonically related to the Gibbs free energy which describes the work obtainable from an isothermal, isobaric process, conditions closely approximated in living systems.

DETAILED DESCRIPTION OF THE INVENTION

Before the present methods and devices for efficiently obtaining information from large numbers of cells are described, it is to be understood that this invention is not limited to particular methods and devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell or sequence" may include a plurality of such cells or sequences and reference to "the well or addresses" may include reference to one or more wells or addresses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Specific Embodiments

Figure 3:
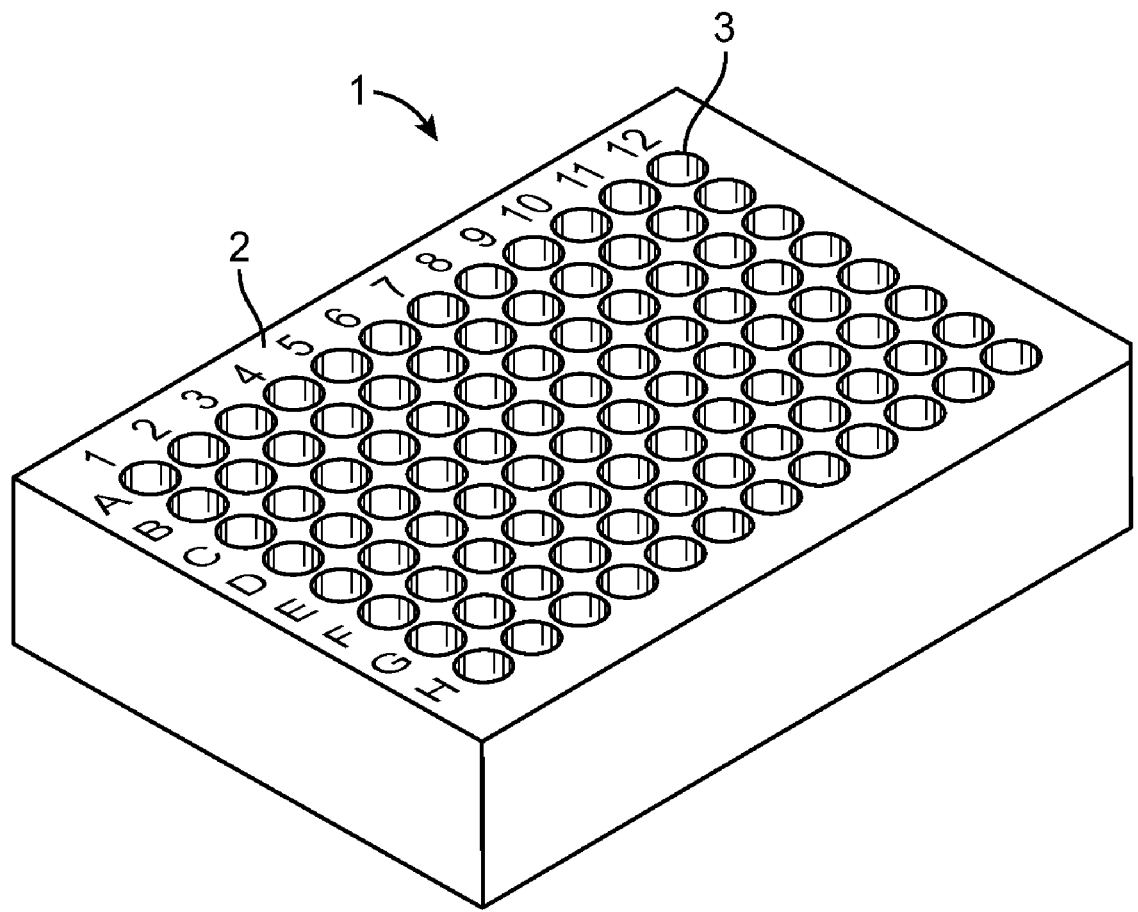
FIG. 3 is a schematic view of embodiment of a multi-well tray component which could be used in connection with the system of the invention.

Referring now to FIG. 3 which shows the multi-well tray component 1 which can be used in connection with the present invention. The tray 1 includes a frame 2 and a plurality of wells 3. As shown in FIG. 3 the wells include indices or addresses 1-12 along the row and indices or addresses A-H along the columns providing a conventional 96 well tray. Although a multi-well tray of this type could be used in connection with the system of the invention, the invention is better suited for trays which include much larger numbers of wells such as trays which include 1,000 or more, 10,000 or more, 100,000 or more, 500,000 or more or 1,000,000 or more wells. Further, the trays of the invention preferably include micro-wells which wells have an opening diameter of less than 1 mm, preferably less than 0.5 mm and may include a volume of approximately 1 picoliter to 500 nanoliters. In one embodiment of the invention the wells each have an opening which is one to five times the diameter of an average human plasma cell which produces antibodies. Micro-wells which have an opening and a volume large enough to hold a single cell and a small amount of liquid and cell growth nutrient can be efficiently used.

The micro-well tray can be comprised of any material and is preferably comprised of a material which can provide a smooth surface such as a high density polymer, glass, silicon or the like. The tray tops described below are comprised of the same or similar materials.

Figure 4:
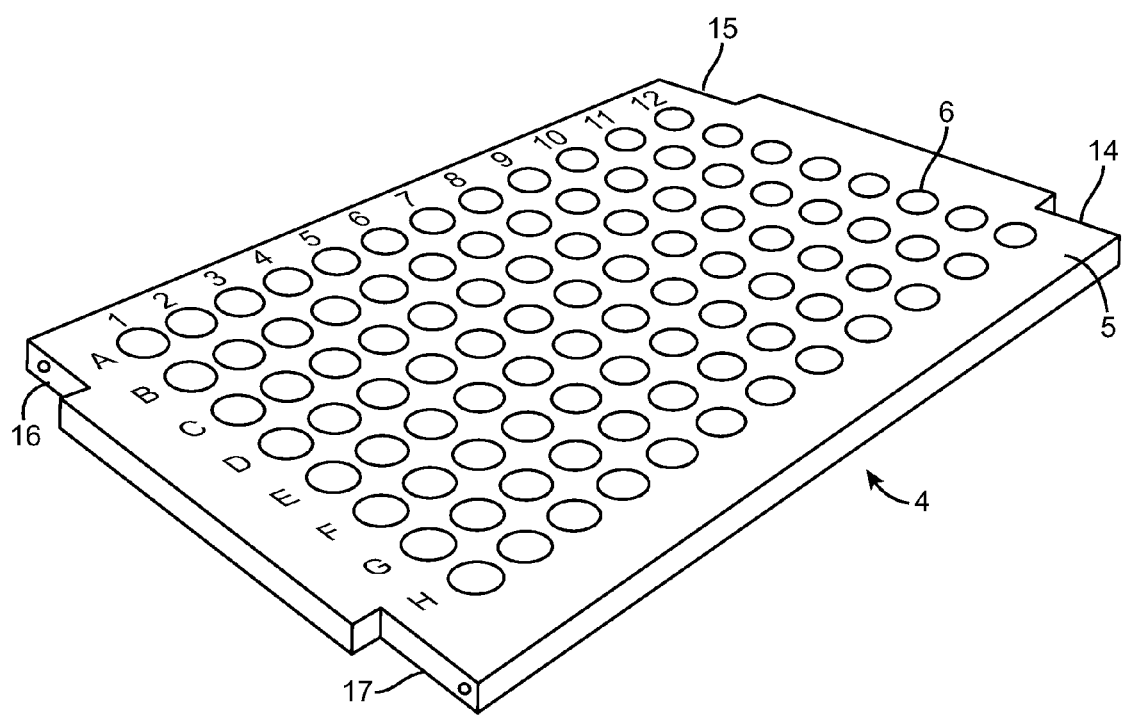
FIG. 4 is a schematic view of a multi-well tray top component which could be used in connection with the present invention.

FIG. 4 is a schematic view of a multi-well tray top 4. The top 4 is comprised of a basic frame 5 and includes a plurality of areas 6 on the top. Each area 6 is addressed with indices as in the multi-well tray 1 of FIG. 3. The areas are numbered 1-12 along the rows and A-H along the columns as with the tray of FIG. 3. Although a multi-well tray of this type could be used in connection with the system of the invention, the invention is better suited for trays which include much larger numbers of wells such as trays which include 1,000 or more, 10,000 or more, 100,000 or more, 500,000 or more or 1,000,000 or more wells. Each of the areas is coated with a binding agent which agent may be covalently bound to the surface of the area. The binding agent may be an antibody binding agent such as a protein or antibody which binds antibodies in general such as Protein A, Protein G, Protein L, anti-IgG Fcγ subclass-specific antibodies, and Protein A/G.

It is desirable that each of the regions or areas of the surface have the binding agent such as an antibody binding agent such as protein A bound to its surface at that region. However, the invention could be carried out when a relatively small percentage of those areas have a protein binding agent bound to its surface. For example, the invention could operate with only 1%, 5%, 10%, 50% or more of the areas on the surface having a binding agent bound thereto. It is desirable that a high percentage, 70% or more, 80% or more, 90% or more, 95% or more or preferably 100% of the areas have a binding agent bound at the region which corresponds to the well or mircrowell. In a similar manner the microwells may have bound to their surface a polynucleotide sequence such as a sequence which specifically binds to a polynucleotide sequence encoding a portion of an antibody or other protein of interest. It is desirable that all of microwells have the polynucleotide bound to a surface. However, the invention can be operative when only a small number of the wells, e.g. 1%, 5%, 10% or more of the microwells have the polynucleotide bound to its surface. It is preferable that when using this embodiment of the invention that a high percentage of the microwells, e.g. 70% or more, 80% or more, 90% or more, 95% or more or more preferably 100% of the microwells have the polynucleotide sequence bound to its surface.

Figure 5:
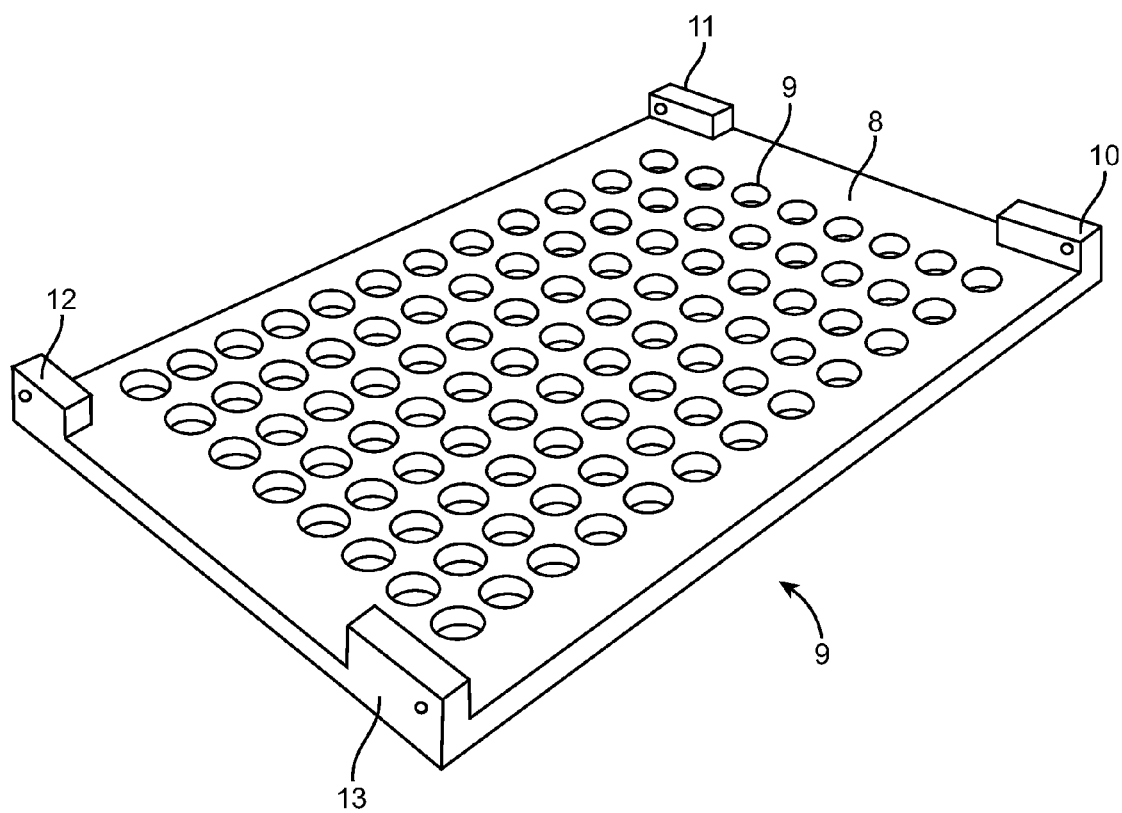
FIG. 5 is a schematic view of a second embodiment of a multi-well tray component which could be used in connection with the top component of FIG. 4.

A second embodiment of the tray is shown in FIG. 5. The tray is comprised of a frame 8 which includes a plurality of wells 9. The tray of FIG. 5 includes upwardly extending notches 10, 11, 12 and 13 in each of the corners. The notches 10-13 fit within the cut-out portions 14, 15, 16 and 17 of the top shown in FIG. 4. In this manner the top and the tray can be precisely aligned with each other.

Figure 6:
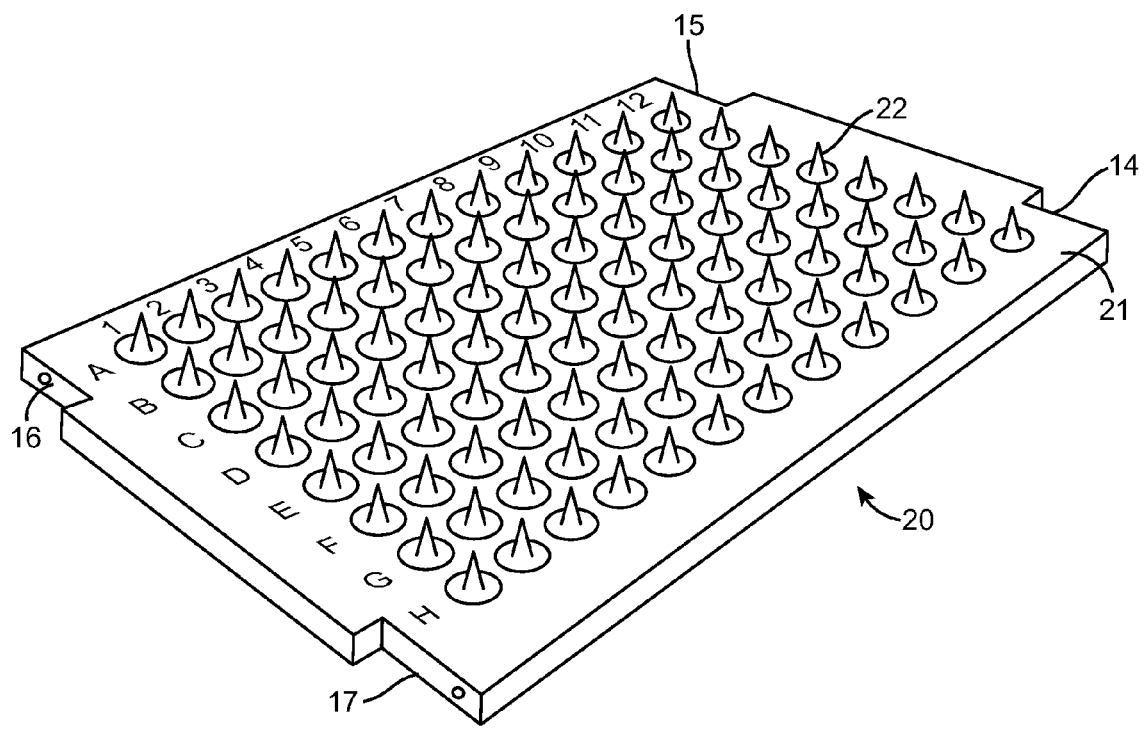
FIG. 6 is a schematic view of a second embodiment of the top which is shown in FIG. 4 wherein the top includes a protuberance on each of the areas.

FIG. 6 shows a tray top 20 comprised of a frame 21 and protuberances 22 on each of the areas corresponding to the well 3 of FIG. 3. In the embodiment shown in FIG. 6 each area includes a single protuberance. However, the area may include 2, 3, 4 or any greater number of protuberances. Each of the protuberances may be coated with a binding agent such as a protein or other amino acid sequence which binds to antibodies. The object of using the protuberances is to provide additional surface area for the binding agent so that as much material such as antibodies can be bound to the binding agent on that surface and extracted from the well.

The embodiments shown in FIGS. 3-6 are simplistic and although useable do not provide the most desired results which can be obtained by dramatically increasing the number of wells and providing other modifications to the system. When the wells are micro-wells it is difficult to see the wells so they must be viewed through some magnification device such as a microscope which magnifies the wells by 10, 50, 100, 200 or more. Such a magnification device may be part of the system of the invention. When viewing the wells through a magnification device it is sometimes difficult to determine which well is actually being viewed. This problem can be addressed to a degree by using different types of indices or different shapes within the wells. The use of different shapes which provides a degree of orientation to the individual viewing the wells is shown within FIG. 8.

The use of the protuberances and notches on the wells and tops shown in FIGS. 4, 5 and 6 can provide for some alignment. This is generally insufficient for devices which include micro-wells present in very high density and very large numbers. The system such as shown within FIG. 7 and described in Example 2 can be used in such situations.

Although the multi-well systems described and shown here are an important invention the use of these systems to obtain information is an important part of the invention. Those skilled in the art will recognize that the following description of the methodology is general in nature. The multi-well systems of the invention can be used in a wide range of different methodologies to extract a wide range of different types of information from a wide range of different cells.

Methodology

Those skilled in the art will recognize that many variations of the multi-well systems described herein can be used to carry out methodology in accordance with the present invention. That methodology involves placing the cells in a large number of wells connected at very high density such as a density of greater than 100 microwells per square centimeter and allowing the cells to produce proteins such as antibodies which are then bound to a binding agent on a surface. The antibodies or proteins are analyzed and the spots on the surface are related to specific wells from which the antibodies or proteins were taken.

The multi-well system can be used in a method for characterizing molecular interactions within a single cell. Central to said method is the confinement of single cells into individual addressable micro-wells. Said micro-wells serve 2 purposes. One is to inhibit the diffusion of reactants and products among individual cells. Second is to accelerate rates for processes such as nucleic acid hybridization or protein interactions. Moreover, said micro-well comprises capture agents that allow efficient capture of the intended macromolecules on a cell by cell basis.

Inside each micro-well, one or a plurality of capture agents each comprise a tag unique to the addressable micro-well where a single cell is confined. When a cell is confined and disrupted, the target macromolecules can be captured rapidly. Subsequent to capture, the means for confinement may optionally be removed to allow manipulation of the captured macromolecules and/or measurement of kinetic properties of the interactions between the captured macromolecules and a labeled ligand. The captured macromolecules such as mRNA can be converted into double stranded (ds) cDNA incorporating said tag identifying its originating micro-well. Said ds cDNA can then be aggregated and processed by massively parallel single-molecule based DNA sequencing technology. During the sequencing process, said micro-well identifying tags are converted into digital tags in the form of a DNA sequence. Said digital tags can then be used to identify and cluster the primary structure of the distinct constituent macromolecules as part of a cis or trans protein complex originating from a single cell.

When fluorescent measurements are taken of cells or surface bound or secreted antibodies, a microarray reader produces an image wherein the intensity of various pixels must be associated with the concentration of cell surface markers, or surface bound antibodies, in specific wells. To insure proper registration between the confined cell, the captured mRNA, and optionally the captured protein, it is desirable to include marker cells with a known cis protein complex into the cell population under investigation.

The system can be tested using a hybridoma cell line that is optionally capable of expressing a surface (e.g. membrane) bound or secreted antibody with known sequence information for both the heavy and light chain. Such lines are deposited and described in the literature and easily acquired. These cells can be stained with an antigen labeled with a distinct fluorophore so they can be identified in the addressable micro-wells. In addition, their respective mRNA will be processed and sequenced so the cDNA sequence plus the digital tags will positively identify the position of the marker cells on the capture microarray slide. On the other hand, the antibody captured on the array can also be stained with the appropriate antigen with the distinct dye to identify its position on the protein array. As such, the position of the marker cells on the microarray slide can be matched with those on the protein array. The mRNA and protein of other cells in the array can be matched based on their position relative to the marker cells, their mRNA and antibodies.

One embodiment of the method of the invention comprises a method of obtaining information from a plurality of isolated cells. The information may be simultaneously obtained from a large number of cells by placing the large number of cells in individual wells. An attempt is made to include a single cell within a single well. However, when carrying out the method involving hundreds, thousands or even tens of thousands of cells and wells it may be that some wells do not include a cell and other wells include more than one cell.

A method of the present invention may begin with immunizing an animal and extracting antibody producing cells from that animal. However, the process may begin with the cells already having been extracted and placing the cells into wells of a well tray. Those skilled in the art will recognize that the methodology of the invention can be carried out in a variety of different ways. In one embodiment a well tray comprised of microwells is used. The microwells have a volume sufficient to accommodate a single cell and liquid nutrient to support the cell for a limited period of time during which the cell produces antibodies. Those skilled in the art will recognize that it is desirable to place a single cell within each microwell. However, when the process is actually carried out some wells will not contain a cell and some wells may contain two or more cells. Although this can limit the effectiveness of the invention, the invention can be carried out when only a small percentage of the microwells contain a single cell, e.g. 1%, 5%, 10%, 50% or more of the cells only contain a single cell and the remainder of the wells contain no cell or a plurality of cells, i.e. 2 or more cells. It is desirable if a very high percentage, 70% or more, 80% or more, 90% or more, or 95% or more of the wells contain a single cell and only a single cell. This makes it possible to utilize all of the wells and specifically relate antibodies produced in the well to a single cell. Those skilled in the art will also recognize that even though it is desirable that all of the cells produce antibodies some of the cells may not produce antibodies or may produce antibodies in insufficient amounts to be detectable. The invention that can be carried out when a relatively small number of the cells are actually producing antibodies. For example, it may be that only 1%, 5%, 10% or 50% of the cells in the wells are actually producing antibodies in detectable amounts even though it is desirable to obtain a high percentage of antibody producing cells, e.g. 70% or more, 80% or more, 90% or more, or 95% or more of the cells placed in wells are producing antibodies. The more wells containing a single cell which is producing antibodies the greater the efficiency of the methodology of the invention.

The cells are cells such as B cells or plasma cells which produce antibodies and the antibodies which are produced in the wells are brought into contact with a binding agent such as protein A which is bound to a surface which may be a membrane. This surface may have a plurality of addressable regions or will include regions which can be specifically relatable to individual wells. The wells may be in a well tray which has a well density of 100 or more wells per $cm^2$ or 1,000 or more wells per $cm^2$ and the wells may include a detectable marker which makes it possible to determine the position of a particular well relative to other wells and the marker may be a marker cell or a group of markers which could include a dye, a nucleotide sequence, a radioactive label or a quantum dot.

After contacting antibodies in the wells with the binding agent a process is carried out to determine binding information relating to the binding of the antibodies which are bound to the surface to an antigen which is preferably a specific known antigen in order to determine information such as the binding affinity of the antibodies to that antigen. The binding information relating to specific areas on the surface is then associated with the particular well in which the antibodies were obtained. Thus, it is possible to simultaneously obtain information from a large number of different wells relating to a large number of different antibodies and associate the antibodies with the wells from which the antibodies were obtained.

After determining particular antibodies on the areas of the surface which are of interest and associating those with the wells of interest it is possible to obtain specific polynucleotide information from the particular wells which information is generally sequence information regarding messenger RNA obtained from particular wells of interest. The messenger RNA may be obtained by binding messenger RNA in the wells to sequences which selectively bind to sequences which encode antibodies such as sequences which encode light and heavy chains of antibodies.

The messenger RNA obtained can be converted to cDNA. The cDNA may contain tags which are specific to the well of particular interest. The tag may be used to associate binding information relating to antibodies of particular interest with messenger RNA from wells of particular interest. The invention is described in further detail below with reference to the figures.

Figure 2:
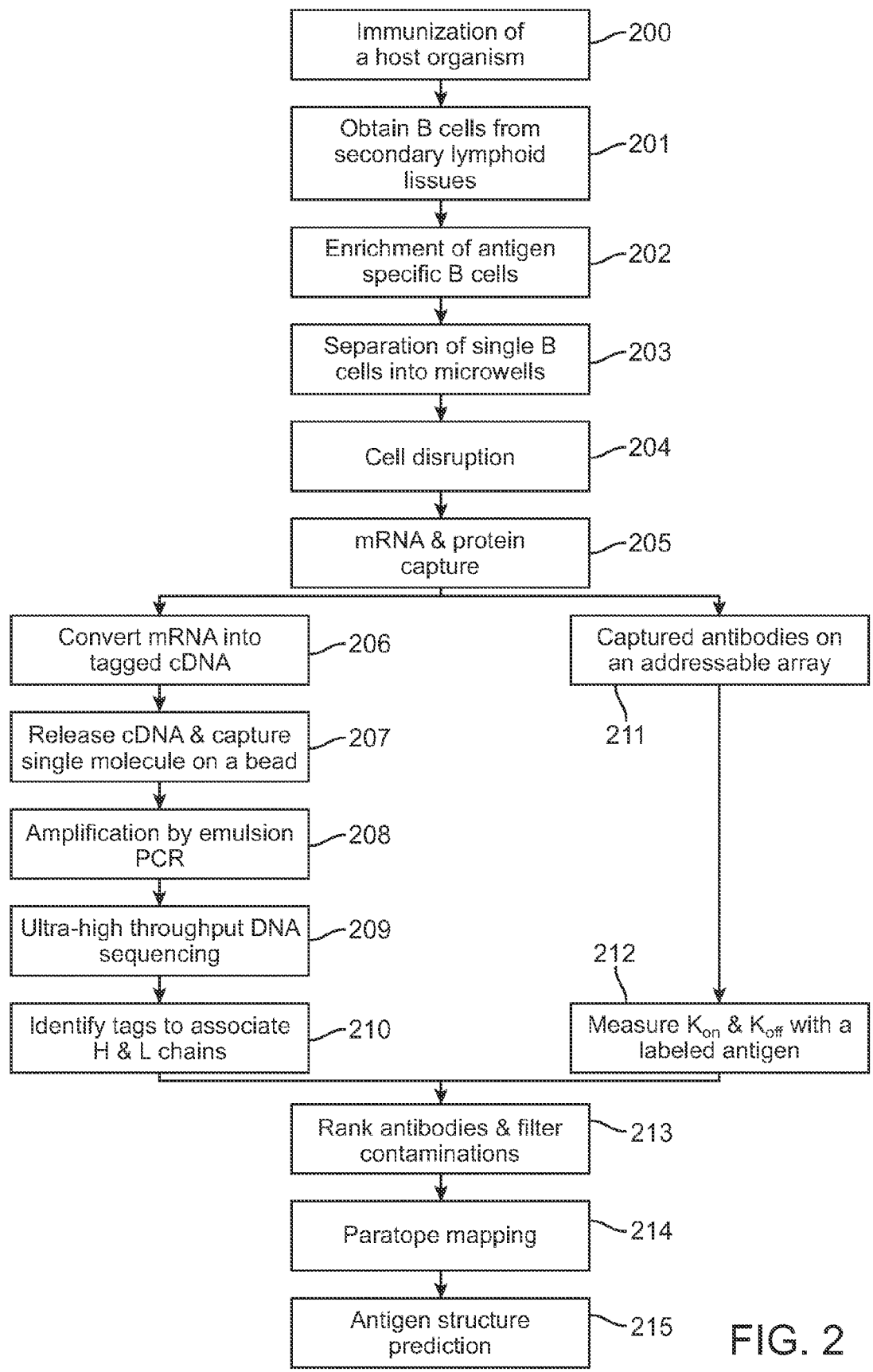
FIG. 2 is a flowchart of a methodology which could be used in connection with the multi-well system of the present invention.

The general methodology of the invention which can be used with the multi-well system following steps shown in FIG. 2. The multiple steps shown in FIG. 2 include the block diagram steps 200-215. Although these steps are carried out in a particular embodiment it is possible to carry out the methodology of the invention using a much smaller number of steps. For example, after immunizing the organism (200) the B cells or plasma cells are obtained and placed into wells (201, 202 and 203). At this point antibodies may be captured on a well top of the device shown in FIG. 4 or 6 (211). Alternatively, before capturing the antibodies the cells may be disrupted (204) and different device tops with different binding agents may be used to capture the messenger RNA (205) and antibodies (211). After capturing the messenger RNA (205) it is subjected to processing steps shown in blocks 206, 207, 208, 209 and 210. The antibodies which are captured may also be subjected to processing in order to determine characteristics such as binding affinity (212). The antibodies may be subjected to further processing (213, 214 and 215).

Although the various steps shown in FIG. 2 can all be utilized in order to enhance the results obtained with the invention the basic concept is to obtain the cells which are to be tested and place those cells into wells. The cells may be plasma cells which make antibodies which can be captured. The same cells can be lysed in order to determine the sequences which are encoding the antibodies produced. Thereby, it is possible to quickly screen a large number of cells for their ability to exhibit a particular characteristic such as producing a desired antibody and at the same time obtain sequence information which is responsible for that characteristic. Those skilled in the art reading this disclosure may conceive of other embodiments which achieve the same or similar results and such embodiments are considered to be within the scope of the present invention.

The methodology can be carried out using trays and lids as shown within FIGS. 3-8. In order to better understand the invention an example of a single micro-well within a tray of the type shown within FIG. 3 is shown in FIG. 1 and described in detail below.

Micro-well 101 of FIG. 1 may have dimensions 50 microns by 50 microns by 50 microns. Dimensions 105 measure 0 to 50 microns from the bottom of micro-well 101 to the top. From one side to the opposite side the dimensions range from −25 microns to 25 microns. A plasmocyte 102 is suspended inside micro-well 101 in a buffered solution that fills the entire micro-well. DNA oligonucleotides are attached to the bottom surface of micro-well 101 in contiguous areas called pads. Pad 103 contains an oligonucleotide complementary to an invariant sequence in the mRNA of plasmocyte 102 that codes for the heavy chain of an antibody. Pad 104 contains an oligonucleotide complementary to an invariant sequence in the mRNA of plasmocyte 102 that codes for the light chain of an antibody. Said invariant sequences are selected so they will bind strongly and physically capture complementary mRNA when said mRNA is released from plasmocyte 102 and diffuses into the solution which may be a cell culture solution in micro-well 101. Whereas micro-well 101 will function properly in any orientation, for the purposes of illustration in FIG. 1 pad 103 and pad 104 are shown attached to the bottom of micro-well 101.

The specific dimensions provided above are only examples. The micro-wells in the trays may vary in size depending on the cell size. Although it is preferable to have wells which include a single cell it is also possible to make the multi-well system of the invention with micro-wells which include multiple cells. The well size can vary from a well which contains up to a milliliter or more of fluid in volume and preferably contains much smaller amounts such as 0.5 milliliter, 0.1 milliliter, 1 picoliter or less or as little as a few hundred nanoliters, e.g. 300 to 900 nanoliters.

In an example disclosed herein, the macromolecules to be analyzed are antibodies produced by cells in a host as an immune response of that host to an antigen. This illustrates an embodiment of the invention as detailed under "ALTERNATIVE EMBODIMENT 2" OR "ALTERNATIVE EMBODIMENT 3" in the "EMBODIMENT" section for determining the structure of 2 constituent macromolecules of a cis protein complex where the 2 copies of each constituent, heavy and light chains, are held together by multiple covalent bonds. In this case, there is a polymorphic difference in the heavy and light chains of each antibody in each B cell generated during the immune response. By practicing the present invention, the combination of the antibody's heavy and light chain primary structure can be determined for each cell analyzed e.g. B cell or plasma cell analyzed. Since such a combination ensures exquisite specificity of the antibody, knowing the primary structure allows one to immortalize the antibody by synthesizing an appropriate construct based on the knowledge of primary structure of the heavy and light chain combination of an antibody and by importing such a construct into an appropriate expression system for unlimited supply of the antibody, which finds diverse applications in a variety of fields including research, diagnostics and therapeutics.

In another embodiment detailed under "PREFERRED EMBODIMENT" or "ALTERNATIVE EMBODIMENT 1", not only the primary structure of the heavy and light chain for each antibody is determined, the antibodies produced by each antibody producing cell such as a B cell are captured to form an addressable array in registration with the micro-wells where the original B cells are each confined. A preparation of fluorescently labeled antigen can be used at varying concentrations to interrogate antibodies captured at each spot such that both the dissociation constant ($k_{off}$) and equilibrium constant ($K_D$) are measured. The association constant can be derived from both $k_{off}$ and $K_D$. Such kinetic binding properties are extremely valuable in ranking the antibodies obtained using the present invention since a large number of antibodies should be recovered in and a means of classifying them is desirable. Furthermore, in the event of an inadequate enrichment for antigen-specific B cells using flow cytometry, these measurements will serve to filter out data deriving from contaminating non B cells or non antigen-specific B cells.

Though the discussion focuses on mouse antibodies, it is clear that the present invention can be applied to antibodies produced by animals with the ability to generate a humoral immune response. In an aspect of the invention a prerequisite for practicing the present invention is the knowledge of the sequence of the constant region for the heavy and light chain mRNA of an antibody for a given isotype. Since the present invention obtains mRNA and proteins directly from antibody producing cells such as B cells, it clearly obviates the need for cell fusion to generate hybridoma cells.

Though the aim to obtain antibodies with the highest $K_D$ and the lowest $k_{off}$ is in line with pharmaceutical development, the present invention can be used to follow an immune response by taking antibody producing cells such as plasma cells and/or antigen specific B cells from any day after immunization. Furthermore, the present invention can be used to monitor the state of the immune system by profiling the B cell population without selection from mouse spleen or even those B cells in circulation for a human subject. This could be very useful in studying autoimmune diseases and to discover biomarkers or potential drug targets. Certainly, the T cell receptors having a structure similar to antibodies can be analyzed in a similar fashion for studying immune functions.

Although only the mouse IgG1, IgG2a, and IgG2b isotype heavy chain conserved sequence and the κ light chain sequence are used for capturing the mouse antibody mRNA in the example illustrated, this represents an embodiment rather than a limitation of the invention. It is entirely within the scope of the present invention to use spotted microarrays wherein a mixture of oligonucleotide probes comprising appropriate sequences can be attached and used to capture all isotypes.

When examining sequences in the example described herein for obtaining antibodies against an antigen, the frequency of occurrence for a given antibody sequence can be used to estimate the $K_D$ of that antibody due to the phenomenon of clonal selection during an immune response. This estimated $K_D$ can be correlated with the measured value obtained from captured antibodies. This line of analysis can aid in understanding the process of affinity maturation in vivo and ultimately guide a focused and more efficient effort to increase the affinity of an antibody in vitro.

Similar to phage display technology, the present invention can be leveraged to screen constructs in many display technologies, such as yeast display, bacterial display, and mammalian display. The candidate display clones can be enriched from the library analogous to the manner for selecting antigen specific B cells by flow cytometry. Once enriched, these display clones can be separated into micro-wells just like antigen specific B cells and processed in a very similar way. A change in the capture sequence has to be made appropriate for the display technology used. However, in contrast to many of these display technologies, we can process candidates much more rapidly and can characterize their binding properties en masse if the proteins expressed by the display clones are captured as described under either "PREFERRED EMBODIMENT" OR "ALTERNATIVE EMBODIMENT 1".

The present invention can be used to investigate cis protein complexes in other cell types. For example, many cell surface receptors responsible for signal transduction possess the ability to form cis complexes with other receptors via non-covalent bonds. It is conceivable to use the present invention to examine these receptors and identify qualitative changes on a per cell basis. In this case, characteristics, such as morphology, surface marker expression, or intracellular marker expression, can be recorded on a per cell basis to be correlated with the sequence information for the receptors under investigation. A cell-by-cell comparison between normal and cancer cells can be envisioned. If the relevant proteins are captured, similar analysis with a labeled ligand of the receptors can be performed to understand the binding characteristics of these cis complexes on a per cell basis as well as to quantify the receptors and to identify different combinations on a per cell basis. All these pieces of information can be correlated with the observed characteristics of the cell mentioned earlier. A high content analysis of the cell and its signal transduction machinery can be performed.

Rare cell populations, such as stem cells, can also be analyzed using the present invention to relate candidate macromolecules with the observed phenotypes on a per cell basis.

With a large number of sequences available for a combination of heavy and light chains of a given antibody, it becomes possible to use the positions of the mutation and the measured equilibrium constant to infer the critical amino acid residues of the paratope on the antibody.

With the critical amino acid residues identified, it also becomes possible to infer the epitopes and the structure around the putative epitopes on the antigen. The present invention estimates the free binding energy of the antibody and the putative protein folding. With the potential epitope identified for each antibody, this provides another criterion to classify the antibody obtained for a target antigen. The ability to quickly identify sets of antibodies each against different epitopes on an antigen is an advantage of the invention. This reduces the number of confirmatory tests required given the large number of different antibodies recovered. Deciphering the structures local to the identified epitopes on the antigen can lead to a good understanding of the overall structure of the antigen when the density of the epitope identified becomes high enough. This outcome is also unprecedented. These are all due to the fact that a large number of antibodies can be rapidly recovered using the invention.

EMBODIMENTS

Preferred Embodiment

Micro-wells may be produced by attaching 50 micron (±25%) high walls onto a flat support or frame and binding oligonucleotides pads inside the wells. Cells are distributed over these micro-wells in such a manner that it allows only a single cell to settle into each micro-well. A cover that is coated with a material suitable for attaching proteins of interest is placed over said micro-wells. For example, to immobilize antibodies on the top cover, the cover is coated with an antibody specific capture agent such as Protein A or Protein L (Sigma-Aldrich, St. Louis, Mo.).

Alternative Embodiment 1

In alternative embodiment 1 a material suitable for attaching proteins of interest is coated on a commercial micro-well array, e.g.: a blank PicoTiterPlate device (454 Life Sciences, Branford, Conn.) containing 50 micron hexagonal wells. Cells are distributed over said hexagonal wells in such a manner that allows only a single cell to settle into each well. For example, to immobilize antibodies on the surfaces of the wells one coats the surfaces with an antibody specific compound such as Protein A. A custom oligonucleotide array (NimbleGen Systems, Inc., Madison, Wis.) is placed over said PicoTiterPlate to capture and tag mRNAs.

Alternative Embodiment 2

In alternative embodiment 2 we fabricate micro-wells by attaching approximately 50 micron walls onto a flat support.

Cells are distributed over said micro-wells in such a manner that allows a single cell to settle into a micro-well. A custom oligonucleotide array (NimbleGen Systems, Inc., Madison, Wis.) is placed over said fabricated micro-wells in order to capture and tag mRNAs. No proteins are captured.

Alternative Embodiment 3

In alternative embodiment 3 a commercial micro-well array, e.g.: a blank PicoTiterPlate device (454 Life Sciences, Branford, Conn.) containing 50 micron hexagonal wells, is used to contain the distributed cells. A custom oligonucleotide array (NimbleGen Systems, Inc., Madison, Wis.) is placed over said commercial micro-well array to capture and tag mRNAs. No proteins are captured.

Alternative Embodiment 4

In this embodiment two planar surfaces are separated a small distance (e.g.: 50 microns±20%) by a porous structure. One or both planar surfaces are microarrays. The porous structure contains holes large enough to contain a biological cell (e.g.: 50 microns). The porous structure is temporarily affixed to one planar surface, thereby constructing an array of open micro-wells. Biological cells are dispersed over the top of said micro-wells in one of two methods: a) stochastic separation, wherein a concentration of said cells is chosen so that only a single cell usually occupies a single micro-well when the cells are randomly dispersed above said micro-wells; and b) deterministic separation, wherein individual cells are caused to move to predetermined micro-wells. After a period of time (e.g.: 3 minutes) cells above micro-wells are allowed to enter said micro-wells due to their increased density. Reagents common to all micro-wells are introduced to the region above said micro-wells and reactions occur within each micro-well. Small molecules are allowed to diffuse out of said micro-wells in a short amount of time (e.g.: 10 seconds). Then the second planar surface is placed over said micro-wells sealing them and allowing reactions inside the micro-wells to occur over a longer period of time. Said reactions result in a modification of the microarray(s) by chemicals confined to said micro-wells. After said microarray(s) are deemed modified, the planar arrays are separated and the porous structure removed. Codes fabricated into said modified microarray(s) are used during analysis to associate micro-wells with measured results. Said codes may be the physical position on a microarray, or a tag caused to be embedded in the analyzed data. For example, in the case of an oligonucleotide array, said embedded tag may be a unique DNA sequence.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Alignment Between DNA Chip and Prefabricated Wells

SU-8 photoresist (MicroChem Corporation, Newton, Mass.) was spin-coated onto a 10 cm silicon wafer in accordance with manufacturer's recommendations. A pattern of 50 micron cubic micro-wells was exposed using ultraviolet light from a mask aligner (SUSS MicroTec AG, Schleißheimer Str. 90, D 85748 Garching b. München) in accordance with manufacturer's recommendations and developed using SU-8 developer (MicroChem). Polydimethylsiloxane (PDMS) (SylGard Elastomer, Ellsworth Adhesives, Germantown, Wis.) was mixed, cured and removed in accordance with manufactuer's recommendations. The bottom tray (FIG. 3) was formed by using a razor blade to cut out an array of 205 by 154 micro-wells (31, 570 micro-wells) and carefully placing it onto a clean and dry microscope slide where it formed a hydrophobic bond with the glass slide. The dimensions and location of the micro-wells exactly matched the location and size of pads of oligonucleotides on a DNA chip (385K CGH array, Roche/Nimblegen, Madison, Wis.). The DNA chip formed the top of the micro-wells (FIG. 4). and was placed above the micro-wells so that most wells were directly beneath DNA and most well walls were in contact with bare glass. When micro-wells this small are used the positioning, alignment, and subsequent sealing of a DNA slide above PDMS wells is sufficiently delicate that mechanical assistance is generally needed, such as a mask aligner or a custom built apparatus.

One example of an available mask aligner is the MJB4 four inch manual mask aligner from SUSS MicroTec AG (Garching, Germany). A glass slide is affixed with mylar tape to a 4" square quartz plate and inserted into the aligner's mask vacuum chuck. PDMS is affixed to a similar plate and inserted into the wafer chuck. The two surfaces are aligned using optics and positioning controls available on the aligner. Once aligned, the PDMS is removed and processing continues until the DNA slide and wells must be aligned. At this time, the PDMS is reinserted into the aligner, the two surfaces (DNA and PDMS) are placed into contact, and the entire assembly is left alone for several minutes while cDNA is constructed from antibody mRNA.

Although this procedure can be carried out it has several drawbacks: 1) The components to be aligned must be pushed into a UV protected area precluding easy access by people and equipment; 2) there are very few places for excess fluid from the necessarily wet cell suspension deposited on top of the wells; and 3) there are expensive features on the aligner that are not needed.

Figure 7:
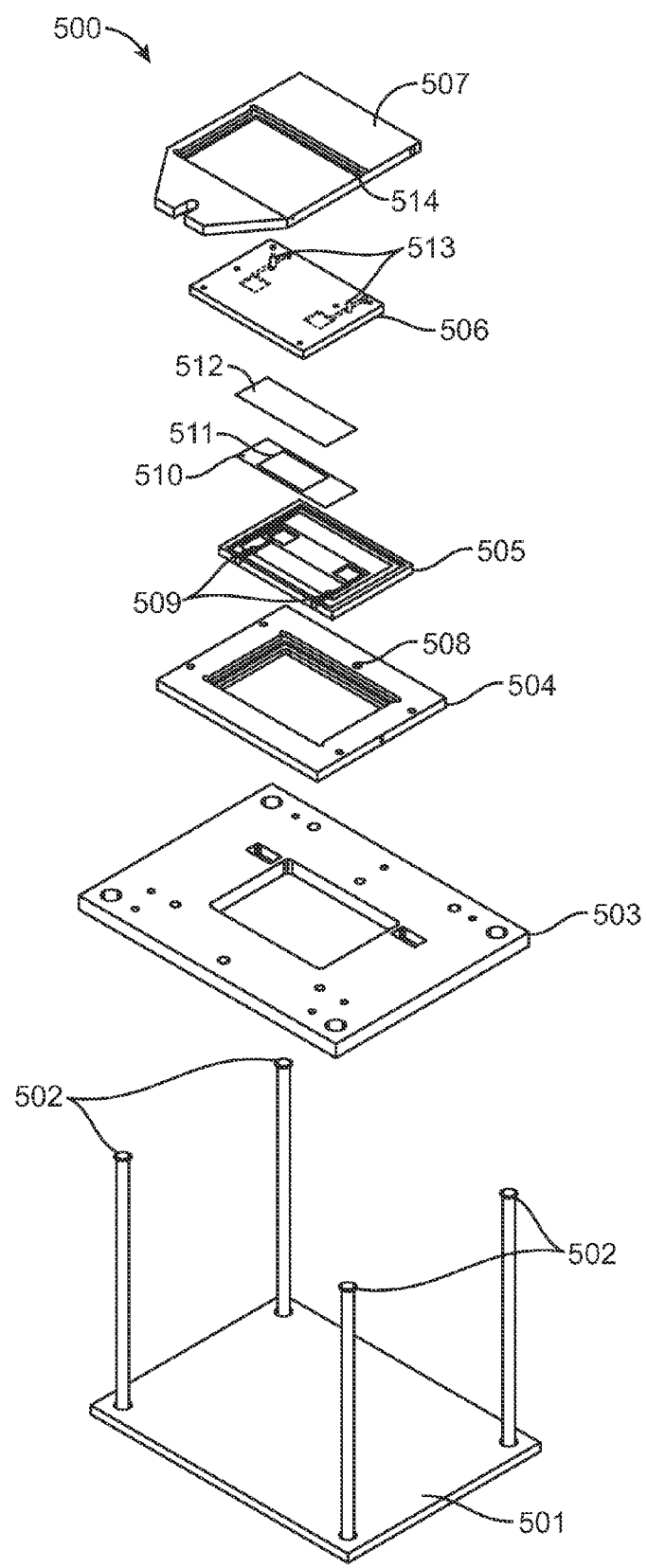
FIG. 7 is an exploded schematic view of a system of the invention showing specific components for aligning the tray with tray tops.

The system can be more efficiently used with a custom aligner designed to contain a small amount of fluid, provide easy access for the experimenter and equipment, while providing a reduced set of functions at a reduced cost. An example of a custom aligner 500 is shown in FIG. 7. Four vertical posts 502 screw into aluminum base plate 501 and support aluminum table 503. On aluminum table 503 sits the bottom pressure plate 504. A first plastic insert 505 and a second plastic insert 506 are sandwiched between bottom pressure plate 504 and top pressure plate 507.

Vacuum port 508 provides close contact between bottom pressure plate 504 and plastic insert 505. Vacuum port 514 provides close contact between top pressure plate 507 and plastic insert 506. The bottom tray includes micro-wells 511 placed on glass microscope slide 510, and the tray is held firmly to the top side of plastic insert 505 by additional vacuum ports 509. Similarly, a DNA chip 512, having the same dimensions as the microscope slide 510, is held firmly to the bottom side of plastic insert 506 by additional vacuum ports 513.

When bottom vacuum is released, the bottom micro-wells 511 and glass slide 510 can be carefully moved together in two axes by sliding them against plastic insert 505. Once the wells 511 are optimally aligned, vacuum is applied to vacuum ports 509 to keep the slide 510 from moving. A small computer interfaced microscope (not shown) is positioned beneath the aluminum table 503 to image cells in wells using flat field light entering the top of apparatus 500.

Once alignment is achieved, marks are placed on the plastic insert 505 to record the position of slide 510. Alternatively, objects are placed next to the glass slide 510 to record the position of the slide 510. Then microwells 511 and the glass slide 510 can be removed, processed and returned to alignment apparatus 500 within a positional accuracy of 10 microns. It was found that 10 micron accuracy was adequate to correctly align the microwells 511 with the DNA chips 512 so that specific addresses on the chip 512 could be correctly matched to specific addresses of the microwells 511.

Example 2

Embedding Numeric Codes in Micro-Well Design

During alignment and processing, it is often useful to examine the micro-wells, or cells in the micro-wells, under a moderate power microscope (e.g.: 100×). The field of view of the microscope seldom encompasses all micro-wells. Therefore, it is difficult to know exactly which wells are being viewed by examining a single microscope image either in real time or afterwards from a captured image. It may be desirable to know exactly which wells are being viewed without having to count wells from an edge or corner.

For this purpose, a coded shape such as a particular shape (FIG. 8) may be embedded into the wells. The shape is a tradeoff between three constraints: 1) the shapes should be different enough that epoxy coated wafers can easily reproduce them and, in turn, they can be seen in the PDMS impressions taken from the epoxy coated wafers; 2) the well volume should not be substantially different from well to well so that cells will experience approximately the same microenvironment; and 3) the wall thickness is not reduced in a manner which would weaken the PDMS structure. Fragments of an octagon provided a useful balance between these constraints. Octagon fragments were separated into symmetric or non-symmetric fragments and used in shapes of FIG. 8.

Figure 8:
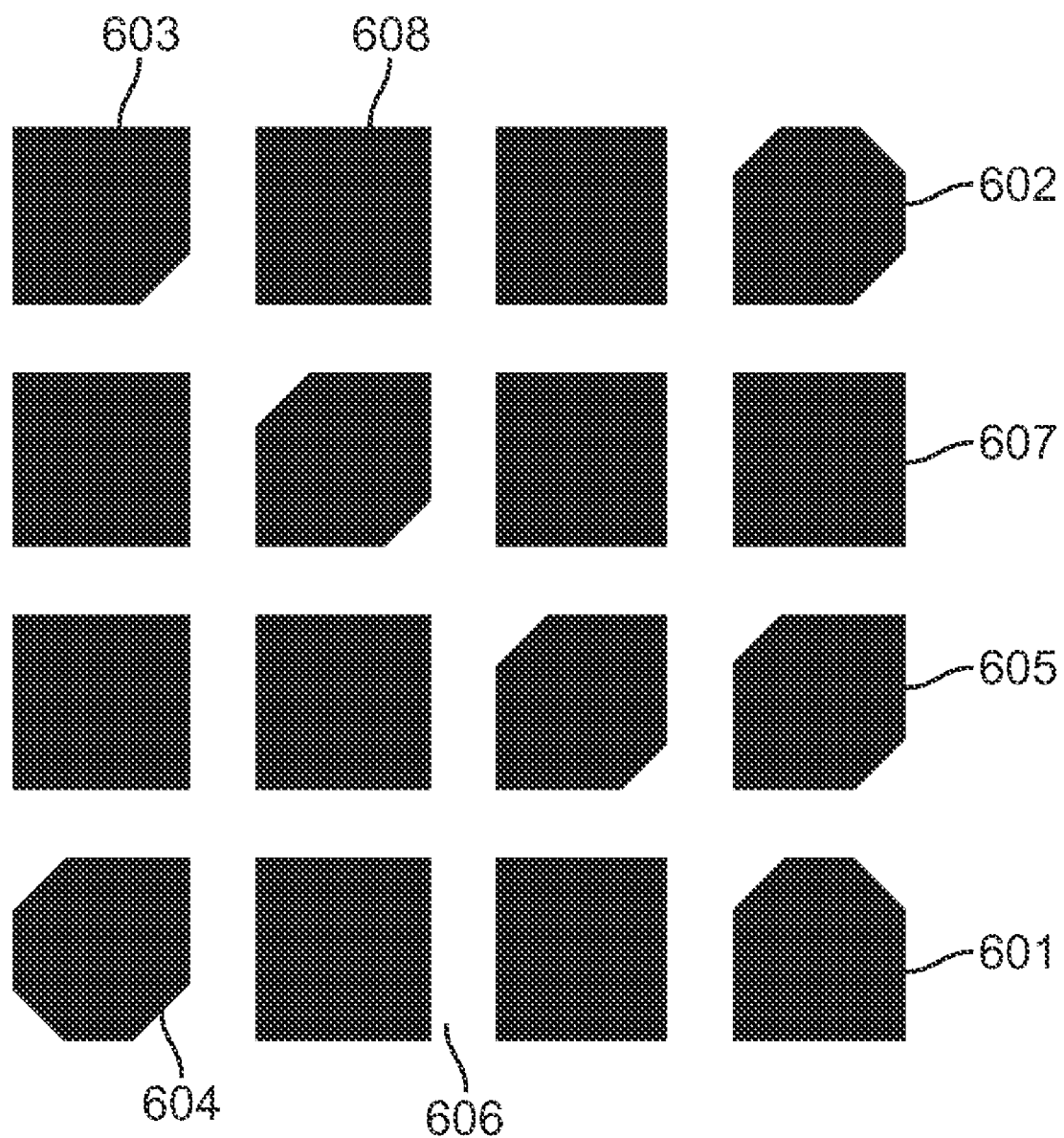
FIG. 8 is a schematic view of micro-wells with different designs and configurations.

In this example a 4×4 block of wells was chosen because under our laboratory microscopes we could easily place 16 wells in the field of view. Referring to FIG. 8, a 16 well block 600 is an example of the use of octagon fragments to embed three numbers in the shape of the wells: 1) the row number; 2) the column number; and 3) the pattern number. In this example, there are a maximum of 64 rows and columns, each numbered 0 through 63. Since there are 4 wells in each row and column per block, this example addresses a maximum of 256 wells in all rows or columns of a pattern. Binary representations are used to encode the row and column numbers. As is well known in computer literature, six binary digits are required to encode values 0 through 63. Symmetrical wells are used to represent row and column 1s and 0s. For example, in FIG. 8, well 605 is a 1 and well 607 is a zero.

Nonsymmetrical wells are used at the corners of the block. Well 601 provides a starting point and starting direction. In addition, the other corners (602, 603 and 604) provide chirality, i.e. the shape is not identical to its mirror image in left and right handed microscopes images viewed from either the top or the bottom. Therefore, a method is needed to determine which wells go with which blocks without presupposing a particular viewing direction. The three corners of the block that are not the start well have a unique orientation that points into the center of the block. Since there are two such orientations (e.g.: well 602 and 603), the two orientations can be used to represent a binary 1 (well 602) and a binary 0 (well 603) in order to encode additional information. In this example, there are different well patterns each with a slightly different dimension so as to accommodate variations in PDMS shrinkage caused by different curing temperatures. The three corners encode for 8 different values, 0 through 7.

FIG. 8 shows a block encoding the three values: column 3, row 4 and pattern 5. The block is first located in a microscope's field of view by finding nonsymetrical well 601 which is designed to have the shape of a home-plate in baseball. Following four wells in the direction of well 601, well 602 defines the chirality of the block, in this case to the left. Wells 603 and 604 confirm this chirality. In addition, starting from the high bit, wells 604, 603 and 602 encode for the binary number 101 which, expressed in decimal, is the well pattern 5.

The column code starts with high bit 606 and ends with low bit 605: 000011, or column 3. The row code starts with high bit 608 and ends with low bit 607: 000100, or row 4.

This is an illustrative example only. The shapes can easily vary to accommodate different designs and materials, as well as the number of wells per block, the sizes and relative arrangements.

Insofar as the description above and the accompanying drawings disclose any additional subject matter that is not within the scope of the claims below, the inventions are not dedicated to the public and the right to file one or more applications to claim additional inventions is reserved.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A multi-well system for characterizing cells, comprising: a tray comprising a plurality of wells, each of the wells comprising a side wall, a bottom and an open top; a first tray top comprising a plurality of areas, each of the areas corresponding uniquely with each well of the tray; a protein binding agent bound to each of the plurality of areas of the first tray top; and a second tray top comprising a plurality of areas, each of the areas corresponding uniquely with each well of the tray, wherein there are oligonucleotide tags bound to the plurality of areas of the second tray top, and wherein the oligonucleotide tags are specific tags that correlate nucleic acids obtained from cells in the wells with a physical location of the wells, are specific to the well of interest and thereby allow pooling of the nucleic acids obtained from cells in the wells for subsequent analysis by ultra-high throughput sequencing.

2. The multi-well system of claim 1, wherein the tray is comprised of 1,000 or more wells fabricated at a density greater than 100 wells per $cm^2$.

3. The multi-well system of claim 1, wherein the protein binding agent is an antibody binding agent and the antibody binding agent is selected from the group consisting of Protein A, Protein G, Protein L, Protein A/G, and anti-IgG Fcγ subclass-specific antibodies.

4. The multi-well system of claim 1, further comprising: an antibody-producing cell bound to a plurality of the plurality of wells in the tray.

5. The multi-well system of claim 1, further comprising: a third tray top comprising a plurality of areas, each of the areas corresponding uniquely with each well of the tray; and a protein binding agent bound to each of the plurality of areas of the third tray top.

6. The multi-well system of claim 4, further comprising: instructions for using the multi-well system to obtain information from antibodies that bind to areas on the first tray top and correlating sequence information from the nucleic acids obtained from the second tray top to the antibody information.

7. The multi-well system of claim 1, further comprising: a plurality of addresses on the tray wherein a unique address is assignable to each well; and wherein 10,000 or more wells are fabricated at a density of 200 wells per $cm^2$ or more.

8. The multi-well system of claim 1, wherein the tray comprises polydimethylsiloxane (PDMS).

9. The multi-well system of claim 1, wherein the tray is comprised of 1,000 or more wells wherein each well holds a volume of from 10 picoliters to 0.1 milliliters.

10. The multi-well system of claim 1, wherein the nucleic acids obtained from cells in the wells encode light and heavy chain variable regions or portions thereof large enough to construct an antibody.

11. A multi-well system, comprising: a tray comprised of a frame and a plurality of wells wherein a plurality of the plurality of the wells has bound to its surface an antibody-producing cell; a first tray top comprising a plurality of areas, each of the areas corresponding uniquely with each of the wells of the tray; an antibody binding agent bound to each of the plurality of areas of the first tray top; a second tray top comprising a plurality of areas, each of the areas corresponding uniquely with each well of the tray; and oligonucleotide tags bound to each of the plurality of areas of the second tray top, wherein the oligonucleotide tags are specific tags that correlate nucleic acids obtained from cells in the wells to a physical location of the wells, are specific to the well of interest and thereby allow pooling of the nucleic acids obtained from the wells for subsequent analysis by ultra-high throughput sequencing.

12. The multi-well system of claim 11, wherein the oligonucleotide tags selectively bind mRNAs which encode antibody light chains or antibody heavy chains.

13. The multi-well system as claimed in claim 12, wherein each of the areas comprise oligonucleotide tags that bind mRNAs that encode antibody light chains and antibody heavy chains.

14. A device to allow optical inspection of cells in a multi-well system, where the multi-well system comprises: a tray comprising a plurality of wells, each of the wells comprising a side wall, a bottom and an open top; a first tray top comprising a plurality of areas, each of the areas corresponding uniquely with each well of the tray; an antibody binding agent bound to each of the plurality of areas of the first tray top; a second tray top comprising a plurality of areas, each of the areas corresponding uniquely with each well of the tray; and an oligonucleotide tag bound to each of the plurality of areas of the second tray top, wherein the oligonucleotide tags are specific tags that correlate the nucleic acids obtained from cells in the wells with a physical location of the wells, are specific to the well of interest and thereby allow pooling of nucleic acids obtained from the wells for subsequent analysis by ultra-high throughput sequencing, wherein the device is capable of aligning the tray and the first tray top and the tray and the second tray top.

* * * * *